United States Patent [19]

Swedberg

[11] Patent Number: 4,931,328

[45] Date of Patent: Jun. 5, 1990

[54] CAPILLARY TUBE WITH REDUCED PROTEIN INTERACTIONS AND CONTROLLABLE ELECTROOSMOTIC FLOW

[75] Inventor: Sally A. Swedberg, Los Altos, Calif.

[73] Assignee: Hewlett-Packard Company, Palo Alto, Calif.

[21] Appl. No.: 234,456

[22] Filed: Aug. 19, 1988

[51] Int. Cl.$^5$ .......................................... B01D 61/42
[52] U.S. Cl. ............................. 428/36.91; 204/299 R; 204/180.1; 204/182.8; 428/426; 428/34.7
[58] Field of Search .............. 204/299 R, 180.1, 182.8; 428/34.7, 36.91, 426

[56] References Cited

U.S. PATENT DOCUMENTS 4,680,201 7/1987 Hjerten ........................... 204/299 R
4,690,749 9/1987 Van Alstine et al. ........... 204/299 R

OTHER PUBLICATIONS

Jorgenson, LuKacs, Capillary Zone Electrophoresis, Science 222 pp. 266–272 (1983).

Primary Examiner—James Seidleck

[57] ABSTRACT

A method for treating capillary walls exposable to protein solutes is provided that reduces interactions of the protein solutes with the wall and that permits control of electroosmotic flow within the capillaries by selection of solution pH. Thus, a capillary tube has an interfacial layer covalently bonded to the inner wall of the tube. This interfacial layer is effective to reduce interactions between the inner wall and protein solutes and preferably includes a hydratable amphoteric phase. The amphoteric phase is a reaction product of a protein, peptide or an ampholyte and an oxygen or nitrogen nucleophile. Electroosmotic flow magnitude and/or flow direction may be controlled when capillaries of the invention are used for electrophoretic separations.

7 Claims, 2 Drawing Sheets

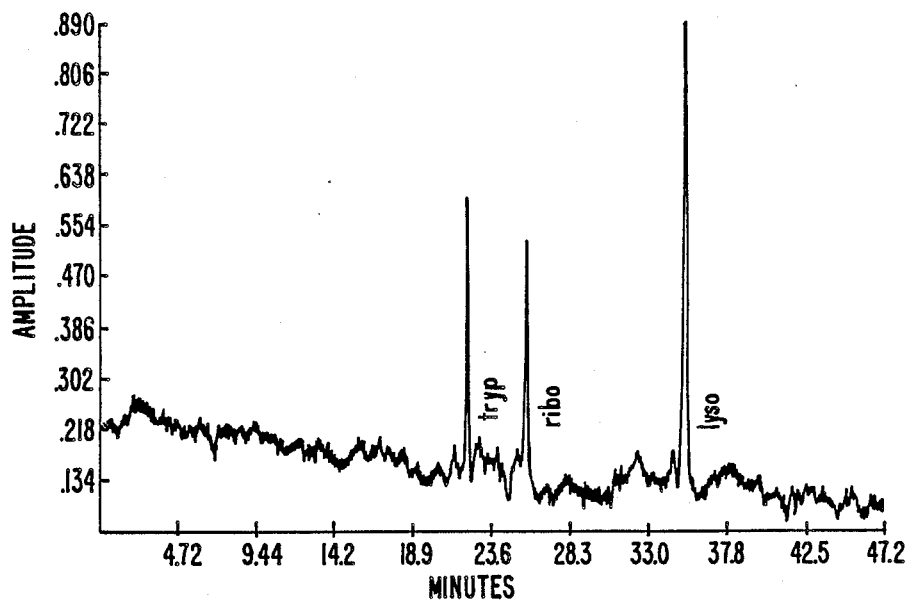
FIG._1.
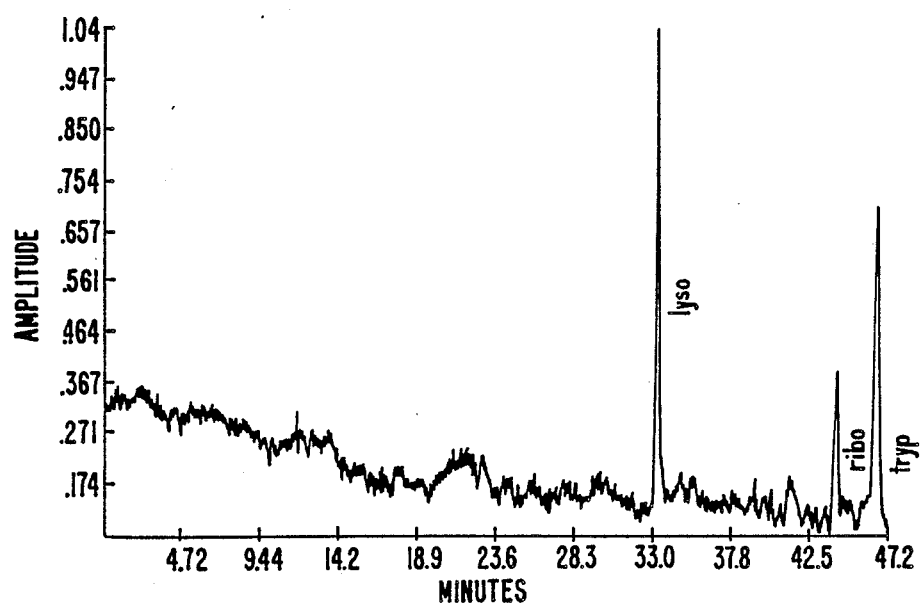
FIG._2.

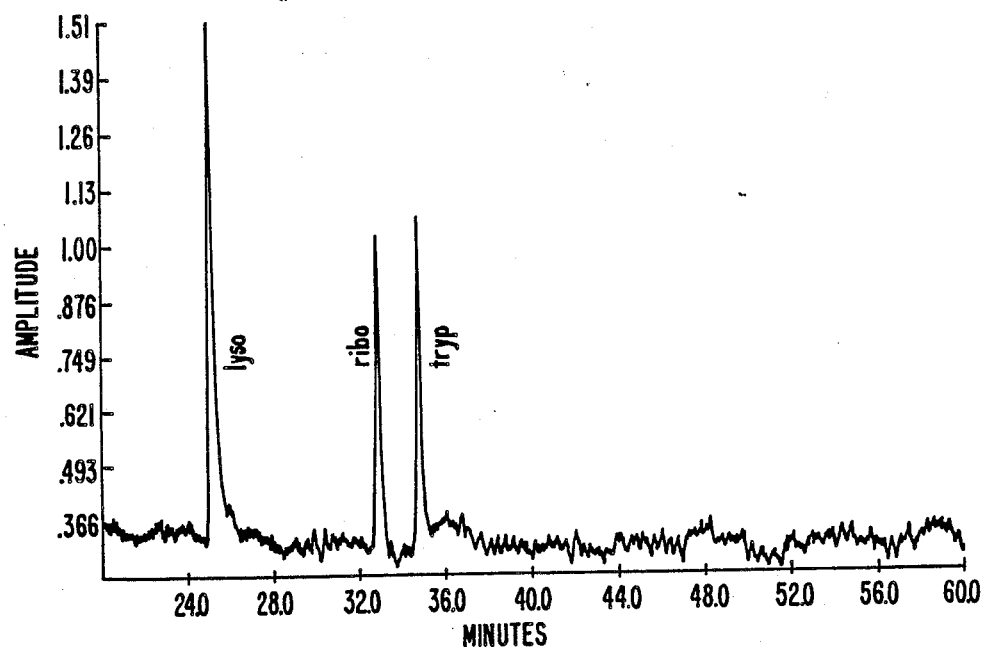
FIG._3.

CAPILLARY TUBE WITH REDUCED PROTEIN INTERACTIONS AND CONTROLLABLE ELECTROOSMOTIC FLOW

FIELD OF THE INVENTION

The present invention generally relates to solid surfaces exposed to protein solutes, and particularly to capillaries used in electrophoretic separations by capillary zone electrophoresis that permit control of electroosmotic flow by selection of solution pH.

BACKGROUND OF THE INVENTION

Capillary zone electrophoresis ("CZE") in small capillaries (less than or equal to 75µ) was first demonstrated by Jorgenson and Lukacs, and has proven useful as an efficient method for the separation of small solutes. *J. Chromatog.*, 218 (1981), page 209; *Anal. Chem.*, 53 (1981), page 1298. The separation process relies upon an electroosmosis effect generally described as the flow of a liquid in contact with a solid surface under the influence of a tangentially applied electric field. Attractive factors for electrophoretic separations by capillary zone electrophoresis are the small sample sizes, little or no sample pretreatment, and the potential for quantification and recovery of biologically active samples.

For example, U.S. Pat. No. 4,675,300, inventors Zare et al., issued June 23, 1987 describes theories and equipment for electrokinetic separation processes employing a laser-excited fluorescence detector. The system described by Zare et al. includes a fused silica capillary with a 75µ inside diameter.

Unfortunately, one of the single greatest disadvantages of capillary zone electrophoresis lies when attempts are made to separate macromolecules such as proteins. Separations of macromolecules by CZE leads to untoward interactions of the biopolymers with the silica capillary wall.

Jorgensen et al. had noted that separation of model proteins, such as cytochrome, lysozyme and ribonuclease A, in untreated fused silica capillaries with a phosphate buffer at pH 7 was accompanied by strong tailing, and suggested this might be caused by Coulombic interactions of the positively charged proteins and the negatively charged capillary wall. Jorgensen et al., *Science*, 222 (1983) page 266.

Lauer et al., *Analytical Chemistry*, 58 (1986), page 166, has reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge. However, disadvantages of this approach are that silica begins to dissolve above pH 7, which shortens column life and degrades performance, only proteins with pI's less than the buffer pH can be analyzed, which drastically reduces the range of useful analysis, and interactions which are not Coulombic may still occur even with proteins bearing a net negative charge due to the complexity of protein composition and structure.

Another approach to the problem of biopolymer, or protein, interactions has been to increase ionic strength. It has been demonstrated that this concept works in principle, but heating is also increased as ionic strength is increased. This heating tends to degrade the efficiency of separation.

Yet another approach to the problem of undesirable protein interactions with the capillary wall has been to coat the electrophoresis tube with a mono-molecular layer of non-crosslinked polymer. Thus, U.S. Pat. No. 4,680,201, inventor Hjerten, issued July 14, 1987 describes a method for preparing a thin-wall, narrow-bore capillary tube for electrophoretic separations by use of a bifunctional compound in which one group reacts specifically with the glass wall and the other with a monomer taking part in a polymerization process. This procedure results in a polymer coating, such as polyacrylamide coating, and is suggested for use in coating other polymers, such as poly(vinyl alcohol) and poly(vinylpyrrolidone). However, this method and capillary tube treatment tends to destroy the electroosmotic flow, and efficiencies are still rather low. These rather low efficiencies suggest that undesirable protein-wall interactions are still occurring.

SUMMARY OF THE INVENTION

It is an object of the present invention to provide capillary tubes that are useful for electrophoretic separations of solutes including macromolecules, with interactions between the solutes and the bore being reduced considerably, and with high efficiencies.

It is another object of the present invention to provide capillary tubes permiting electroosmotic flow control, such as control of flow magnitude and/or flow direction.

Further objects and advantages of the invention will become apparent to those skilled in the art upon examination of the specification and appended claims, as well as in practice of the present invention.

In one aspect of the present invention, an interfacial layer is covalently bonded to the inner wall of the capillary tube. The interfacial layer is effective to reduce interactions between the inner wall and protein solutes, and includes a hydratable amphoteric phase. This amphoteric phase has a determinable isoelectric point and permits electroosmotic flow control by selection of solution pH.

In another aspect of the present invention, the interfacial layer, or reduced interaction phase, includes an ionizable species having an acidic equilibrium or a basic equilibrium. The ionizable species permits electroosmotic flow control by pH selection.

Capillary tubes as described by the present invention have been prepared and used in highly efficient separations for various protein mixtures with good reproducibility and consistent performance upon repeated use.

BRIEF DESCRIPTION OF THE DRAWINGS

FIGS. 1 and 2 illustrate electropherograms of the same protein mixture on a capillary of the invention, but with the FIG. 1 separation having been run at pH 5 and FIG. 2 at pH 7; and FIG. 3 illustrates an electropherogram of the same protein mixture as in FIGS. 1 and 2, but on another capillary tube of the invention.

DETAILED DESCRIPTION OF THE PREFERRED EMBODIMENTS

The present invention provides a solid surface that is modified so as to have reduced interactions with protein solutes. One particularly preferred application is for small bore capillary tubes, such as the tubes used in capillary zone electrophoresis. These tubes are usually less than 500μ, more typically about 20μ to about 200μ, in internal diameter. Other applications include medical uses, such as heart-lung machines and implants, where surfaces are exposed to protein solutes. For convenience, reference will hereinafter be to a small bore (less than about 500 microns) capillary tube with the bore having been modified in accordance with the invention.

The modification is whereby a reduced interaction phase is covalently bonded along the bore, or inside wall, as an interfacial layer between the inside wall of the capillary and the protein solutions when in use. The reduced interaction phase of such coating is effective to reduce interactions between protein solutes and the bore, preferably while permitting reasonably high electroosmotic flow and resulting in excellent efficiencies. When this interfacial layer is about four to about six molecular layers thick, then it has been found that electroosmotic flow is reasonably high in use for capillary zone electrophoresis; however, fewer molecular layers (so long as at least one) or greater molecular layers are possible, and may be desirable for particular applications. When bulk molecular layers are coated on the surface, the electroosmotic flow tends to substantially decrease, which is normally not desired in a system with a single detector with species which migrate towards two electrodes.

Two preferred embodiments of the inventive modified surface will now be described. The first embodiment is where the reduced interaction phase includes an ionizable species having an acidic equilibrium or a basic equilibrium. Preferred ionizable species with a basic equilibrium are amino groups. Preferred ionizable species with an acidic equilibrium are carboxyl groups. When the ionizable species is an amino group, then control of electroosmotic flow magnitude and direction may be selected by the pH of solution being passed through the capillary tube. Where the ionizable species is a carboxyl group, then electroosmotic flow magnitude may be controlled by pH of the solution.

Preparation of both ionizable species types is as follows. When the capillary bore, or inner wall, surface to be modified is silica based, it is first hydrated and then reacted with an organo- or chlorosilane having two functional end groups. Concentrations of silylating reagent in aqueous solution from about 0.1 wt. % to about 1 wt. % result in about four to six molecular layers being bonded to the surface. These about four to six layers are preferred to ensure there are no remaining unreacted silanol groups, but still permit a substantial electroosmotic flow. The unreacted functional group of the silylating reagent is a nitrogen nucleophile or an oxygen nucleophile. The nitrogen nucleophile provides amino groups for ionizable species having a basic equilibrium. Alternatively, the nitrogen nucleophile may be converted to carboxyl groups, as further described hereinafter. The oxygen nucleophile (e.g., hydroxyl groups) may be converted to carboxyl groups as ionizable species having an acidic equilibrium, as further described hereinafter.

Exemplary silylating reagents are 3-aminopropyl trimethoxysilane and 3-aminopropyl triethoxysilane. Other suitable silylating reagents for surfaces desired to have nitrogen nucleophiles include:
4-aminobutyldimethylmethoxysilane,
4-aminobutyltriethoxysilane,
(aminoethylaminomethyl)phenethyltrimethosysilane,
n-(2-aminoethyl)-3-aminopropylmethyldimethoxysilane,
n-(2-aminoethyl-3-aminopropyl)trimethoxysilane,
n-2-aminoethyl-3-aminopropyltris(2-ethylhexoxy)silane,
6-(aminohexylaminopropyl)trimethoxysilane,
aminomethyltrimethylsilane,
p-aminophenyltrimethoxysilane,
aminophenyltrimethoxysilane,
3-(1-aminopropoxy)-3,3-dimethyl-1-propenyltrimethoxysilane,
3-aminopropyltris(methoxyethoxyethoxy)silane,
3-aminopropyldimethylethoxysilane,
3-aminopropylmethyldiethoxysilane,
3-aminopropyltris(trimethylsiloxy)silane, and
ŗaminoundecyltrimethoxysilane.

Silylating reagents yielding oxygen nucleophiles include:
3-glycidoxypropyltrimethylethoxysilane,
(3-glycidoxypropyl)methyldiethoxysilane,
3-glycidoxypropylmethyl-di-isopropenoxysilane, and
(3-glycidoxypropyl)trimethoxysilane.

As may be understood from the illustrative silylating reagents for surfaces desired to have nitrogen nucleophiles, the unbonded end of the reagent has an amino group. These amino groups are ionizable species with a basic equilibrium. Thus, for example, a surface to which 3-amino-propyltrimethoxysilane has been bonded has primary amino groups as ionizable species with a basic equilibrium of about pKa 9. Conversely, a silylating reagent yielding an oxygen nucleophile would be prepared by reacting acetic anhydride with 3-glycidoxypropyltrimethylethoxysilane for an acidic equilibrium of about pKa 4.

Use of amino groups as the ionizable species permits control of electroosmotic flow magnitude and direction. Use of carboxyl groups as the ionizable species permits control of electroosmotic flow magnitude. Amino groups themselves can be reacted with a reagent such as succinic anhydride to form the carboxyls, when one wishes a carboxyl group as the ionizable species. The flow controls with either type of ionizable species are achieved by selection of solution pH during electrophoretic separations of proteins in solution.

While the invention may be practiced with the first embodiment, more precise electroosmotic flow control can be achieved with second embodiment capillary tubes. The second embodiment is preferably derived from the first embodiment, as will now be more fully described.

Second embodiment capillary tubes have an interfacial layer that includes a hydratable amphoteric phase, prepared by reacting (that is, covalently bonding, or coupling) a protein, peptide or an ampholyte with the oxygen or nitrogen nucleophiles as previously described. The amino groups (of the nitrogen nucleophile) and the carboxyl or hydroxy groups (of the oxygen nucleophile) are activated to effect the coupling. For example, the amino groups may be activated with gluteraldehyde or carbonyldiimidazole, and the carboxyl or hydroxy groups with carbonyldiimidazole. Alternatively, the proteins, peptides and ampholytes themselves may be activated to effect the coupling. For example, dipeptides may be activated with gluteraldehyde while other, larger chain peptides and ampholytes may be activated with carbodiimide. Such activation for coupling proteins, peptides or ampholytes are well known in the art.

Suitable proteins, peptides and ampholytes for inclusion in the covalently bound interfacial layer have a molecular weight between about 200 daltons to about 58K daltons. That is, molecules in size from dipeptides to macromolecules can be utilized. Ampholytes are particularly preferred because these synthetic molecules are commercially available for particular, narrow pI ranges. As is known, ampholytes may be synthesized by copolymerization of amines and amino acids with epichlorohydrin. By a suitable choice of amines and amino acids, a large part of the buffer capacity can be concentrated into a narrow pH-interval (2-3 pH units). Ampholytes are commercially available from sources such as Pharmacia Fine Chemicals (under the trade name "Pharmalyte") and from Bio-Rad Laboratories (under the trade name "Bio-Lyte").

The amphoteric phase, whether protein, peptide or ampholyte, includes ionizable cationic and ionizable anionic species. The cationic species include amino, guanidinium, imidiazolium and mixtures thereof. Amino species for the cationic species may be obtained from lysine side chains, guanidiminium may be obtained from arginine side chains, and imidiazolium from histidine. The anionic species of the amphoteric phase has carboxyl groups from aspartic acid and glutamic acid side chains. The synthetic ampholytes have ionizable cationic species from amino groups, most of which are tertiary, but a few being secondary or primary. The anionic species is provided by carboxyl groups of two kinds: $\alpha$-amino carboxylic groups and carboxyl groups from polymerized glycylglycin.

The proteins, peptides and ampholytes suitable for forming the amphoteric phase are all highly hydrated under use conditions. This is important for reversability of interactions (albeit reduced) between the coated surface and the protein solutes. This hydratable amphoteric phase permits control of both electroosmotic flow magnitude and flow direction. Control over the electroosmotic flow magnitude means that efficiencies can be optimized for particular separations. Control over flow direction means that the elution order can be modified, and indeed can be reversed. Reversibilty of electroosmotic flow means that a protein that would normally be resolved very slowly can be eluted earlier.

Coatings of the invention have resulted in protein separations with efficiencies in the range of 300,000 to about 1,000,000 theoretical plates. These highly efficient separations have been accomplished with very low protein to wall interactions (k'), usually less than 0.02. The electroosmotic flow rates at these very low k' values and high efficiencies are believed to be about optimum for maximum efficiencies.

EXPERIMENTAL

The following examples, methods, materials and results are described for purposes of illustrating the present invention. However, other aspects, advantages and modifications within the scope of the invention will be apparent to those skilled in the art to which the invention pertains.

Example I illustrates the preparation of first embodiment tubes. Example II illustrates the preparation of second embodiment tubes.

EXAMPLE I

Silica capillary tubing (Polymicro Technologies) of 50$\mu$ I.D. was cut into 100 cm lengths. Individual capillary tubes were then prepared by covalently bonding a four to six molecular layered, reduced interaction phase terminating in an amino, ionizable species as follows:

The silica capillary was was first hydrated with 0.1 N NaOH by pumping through the capillaries at a rate of about 1-2 $\mu$l/minute. The wash was continued for an 8-10 hour period. The capillaries were then washed for 2-3 hours with DI water.

The walls were then reacted with 3-aminopropyltrimethoxysilane (3-APTS). A 1% solution of 3-APTS was prepared and adjusted to pH 4.5 with acetic acid. This solution was pumped through the capillaries at a rate of 1-2 $\mu$l /minute for one hour in one direction, then the ends were reversed and the reagent was pumped in the opposite direction for another hour. The capillaries were then attached to a manifold connected to a helium tank, and were cured overnight with a flowing stream of helium.

Referring to FIG. 1, a column as just described was utilized to separate a mixture of lysozyme, ribonuclease and trypsinogen at pH 5 (98 cm to detector, 200 mM OAc, 200 v/cm). However, when the same protein mixture was separated at pH 7 (shown by FIG. 2 (98 cm to detector, 200 mM Pi, 50 v/cm)), then the peaks lyso and tryp reversed in elution order. Thus, a comparison of FIGS. 1 and 2 shows the use of an inventive capillary tube in permitting control of electroosmotic flow by selection of solution pH.

EXAMPLE II

General

Silica capillary tubing of 50 I.D. cut into 100 cm lengths with attached 3-APTS was prepared as in Example I. The amino groups were activated with a five percent glutaraldehyde solution in 0.1 N phosphate buffer, pH 7.0, by passing the solution through each end of the capillaries for one hour each direction. The ends were sealed and the capillaries were allowed to sit for one hour at room temperature. Excess glutaraldehyde was then washed away by passing a 0.1 M phosphate buffer, pH 7.0, through the columns for one hour at flow rates of 1-2 $\mu$L/min.

Solutions of the desired hydratable amphoteric compounds were then prepared as 0.2 mM concentrations in 0.1 M phosphate buffer, pH 7.0. The ends of the were sealed, and the columns were allowed to sit for a minimum of two hours at 4° C. in order to form a reaction product of the protein, peptide or ampholyte with the activated oxygen or nitrogen nucleophile. The excess, unreacted amphoteric compounds were then washed away at flow rates of 1-2 mL/minute for approximately 2-3 hours with the appropriate starting buffer.

Protein

Lactalbumin was attached as the hydratable amphoteric phase as described above, and then was tested for electroosmotic flow (EOF) rate at various pH values. Table I, below, sets out the EOF data with a buffer of pH 7.0, 20 mM pyrophosphate and 10 mM KCl at 300 v/cm.

TABLE I

| pH | EOF mm/sec | N |
|---|---|---|
| 4.0 (anodic) | 0.68 | $2.2 \times 10^4$ |
| 5.5 | 0 | — |
| 7.0 (cathodic) | 1.06 | $2.6 \times 10^5$ |
| 8.6 (cathodic) | 1.40 | $2.6 \times 10^5$ |

As seen by the data of Table I, use of this inventive capillary (second embodiment) permited control of both electroosmotic flow and magnitude by selection of solution pH. The data also shows the very high efficiencies achievable.

Dipeptide

The dipeptide glycyl-phenylalanine amide was similarly attached to capillaries and used to separate the protein mixture described in Example I. FIG. 3 (200 mMPi, pH 6.8, 96 cm to detector, 200 v/cm) illustrates the excellent separation achieved with these usually difficult proteins.

EXAMPLE III

Capillaries prepared as in Example I were washed thoroughly (500 ml at 1-2 μL/min) with dry dioxane. A 0.2 M solution of carbonyldiimidazole in dry dioxane was pumped through the capillaries at a rate of 1-2 μl/min for one-half hour. The ends were sealed and the capillaries were allowed to sit 1-2 hours. The capillaries were washed out with dry dioxane (500 μl) at the previously stated flow rates to get rid of excess unreacted carbonyldiimidazole. A 40% solution of Pharmalyte 4-6.5 was pumped through the activated capillaries for one-half hour at 1-2 μl/min. The capillaries were allowed to sit for 1-2 hours and were then washed with dI water overnight.

Table II, below, compares the just described capillaries with the Example I capillaries.

TABLE II

| COLUMN | ELECTROOSMOTIC FLOW RATE (mm/sec) | |
|---|---|---|
| | CATHODE* | ANODE** |
| Example III | 0.35 | 0.44 |
| Example I | 0.53 | 0.92 |

*Done in 200 mM phosphate buffer pH 6.8 at 150 v/cm.
**Done in 200 mM acetate buffer pH 4.0 at 200 v/cm.

Examples II and III illustrate preparation of second embodiment capillaries by activating the first embodiment capillaries (here illustrated with amino groups) and then coupling the protein, dipeptide and ampholyte respectively therewith. Example IV illustrates the converse.

EXAMPLE IV

The number of reactive carbonyls in Pharmalyte 4-6.5 were determined based on the description of Pharmalyte by Soderberg et al. and determined to be 1.5 N. (Soderberg et al., in "Protides of the Biological Fluids", H. Peeter, ed., Permagon Press, Oxford, 1979, p. 687.) To 2 mL. of Pharmalyte 4-6.5, 0.6 gm ethyl (N,N,dimethylaminopropyl) carbodiimide (EDAC) was slowly added and the pH of the solution was maintained below pH 6.0. After the last of the EDAC was added and the pH was stable, the activated Pharmalyte solution was pumped through the amino phase capillaries (prepared as in Example I) at 500 μl for 1-2 minutes. The capillary ends were capped and placed at 4° overnight. The capillaries were washed thoroughly with water then equilibrated to running buffer and were ready for use.

In summary, capillary tubes of the invention permit electroosmotic flow magnitude and/or flow direction simply by selection of solution pH. These tubes may be used in highly efficient separations of various protein mixtures.

Although the present invention has been described with reference to specific examples, it should be understood that various modification and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

It is claimed:

1. A capillary tube defining an inner wall, useful for electrophoretic separations of proteins in solution, comprising:
an interfacial layer covalently bonded to the inner wall and effective to reduce interactions between the inner wall and protein solutes, the interfacial layer including a hydratable amphoteric phase, the amphoteric phase being a reaction product of a protein, a peptide or an ampholyte and an oxygen or nitrogen nucleophile.

2. The capillary tube as in claim 1 wherein the amphoteric phase has a determinable isoelectric point and selectively permits electroosmotic flow control.

3. The capillary tube as in claim 2 wherein the electroosmotic flow control is selected by solution pH.

4. The capillary tube as in claim 3 wherein the amphoteric phase permits control of electroosmotic flow magnitude.

5. The capillary tube as in claim 3 wherein the amphoteric phase permits control of electroosmotic flow direction.

6. The capillary tube as in claim 1 wherein the amphoteric phase includes ionizable cationic and ionizable anionic species, the cationic species selected from the group consisting of amino, guanidinium, imidazolium and mixtures thereof, the anionic species being carboxyl groups.

7. The capillary tube as in claim 6 wherein the amphoteric phase has a buffer capacity within a pH-interval of about 2 or 3 pH units.

* * * * *